US012807557B2

United States Patent
(12) United States Patent
Iwase et al.

(10) Patent No.: US 12,807,557 B2
(45) Date of Patent: Nov. 24, 2026

(54) METHOD FOR PRODUCING FLUORINATED ETHER COMPOUND

(71) Applicant: AGC INC., Tokyo (JP)

(72) Inventors: Takuya Iwase, Tokyo (JP); Motoshi Aoyama, Tokyo (JP)

(73) Assignee: AGC Inc., Tokyo (JP)

(*) Notice: Subject to any disclaimer, the term of this patent is extended or adjusted under 35 U.S.C. 154(b) by 839 days.

(21) Appl. No.: 18/102,141

(22) Filed: Jan. 27, 2023

(65) Prior Publication Data

US 2023/0174446 A1 Jun. 8, 2023

Related U.S. Application Data

(63) Continuation of application No. PCT/JP2021/033804, filed on Sep. 14, 2021.

(30) Foreign Application Priority Data

Sep. 16, 2020 (JP) ................................ 2020-155282

(51) Int. Cl.

| | |
|---|---|
| ***C07C 43/12*** | (2006.01) |
| ***C07C 41/34*** | (2006.01) |
| ***C07C 303/44*** | (2006.01) |
| ***C07C 309/80*** | (2006.01) |

(52) U.S. Cl.

CPC ............ *C07C 43/126* (2013.01); *C07C 41/34* (2013.01); *C07C 303/44* (2013.01); *C07C 309/80* (2013.01)

(58) Field of Classification Search

CPC ...... C07C 41/34; C07C 303/44; C07C 303/90
See application file for complete search history.

(56) References Cited

FOREIGN PATENT DOCUMENTS

| | | | | |
|---|---|---|---|---|
| JP | 2017088551 | A | 5/2017 | |
| JP | 2017137509 | A | 8/2017 | |
| WO | WO-2015022871 | A1 | 2/2015 | |
| WO | WO2019/044479 | A1 * | 3/2019 | ........... C08G 65/336 |

OTHER PUBLICATIONS

International Search Report issued Dec. 21, 2021 in PCT/JP2021/033804 (with English translation), 6 pages.

* cited by examiner

*Primary Examiner* — Paul V Ward
(74) *Attorney, Agent, or Firm* — Element IP, PLC

(57) ABSTRACT

To provide a method for producing a fluorinated ether compound having a poly(oxyfluoroalkylene) chain and a sulfonate group with low impurity content and in high yield. A method for producing a fluorinated ether compound, comprising step 1 of sulfonylating a fluorinated ether compound having a poly(oxyfluoroalkylene) chain and a hydroxy group in the presence of a fluorinated solvent, a base and a sulfonylating agent to obtain a product containing a fluorinated ether compound having a poly(oxyfluoroalkylene) chain and a sulfonate group, and step 2 of contacting the product obtained in step 1 with an adsorbent having a pH of at most 8.0.

7 Claims, No Drawings

METHOD FOR PRODUCING FLUORINATED ETHER COMPOUND

TECHNICAL FIELD

The present invention relates to a method for producing a fluorinated ether compound.

BACKGROUND ART

A fluorinated ether compound having a poly(oxyfluoroalkylene) chain and a reactive silyl group is suitably used for a surface treatment agent because it can form a surface layer that exhibits high lubricity, water and oil repellency, etc. on the surface of base material.

In synthesizing such a fluorinated ether compound, it is known to use an intermediate obtainable by reacting a fluorinated ether compound having a poly(oxyfluoroalkylene) chain and a hydroxy group with a sulfonylating agent such as trifluoromethanesulfonic anhydride (Patent Document 1).

PRIOR ART DOCUMENT

Patent Document

Patent Document 1: JP-A-2017-137509

DISCLOSURE OF INVENTION

Technical Problem

When the present inventors examined the procedure described in Patent Document 1, they found that the obtained product contained a large amount of impurities and that further improvement was necessary.

Therefore, the present invention has an object to provide a production method that can produce a fluorinated ether compound having a poly(oxyfluoroalkylene) chain and a sulfonate group, with low impurity content and in high yield.

Solution to Problem

The present inventors have found that the above object can be accomplished by the following constructions.

(1) A method for producing a fluorinated ether compound, comprising
 step 1 of sulfonylating a fluorinated ether compound having a poly(oxyfluoroalkylene) chain and a hydroxy group in the presence of a fluorinated solvent, a base and a sulfonylating agent to obtain a product containing a fluorinated ether compound having a poly(oxyfluoroalkylene) chain and a sulfonate group, and
 step 2 of contacting the product obtained in step 1 with an adsorbent having a pH of at most 8.0.

(2) The method for producing a fluorinated ether compound according to (1), wherein no water washing treatment is performed on the product obtained in step 1 between the end of step 1 and the end of step 2.

(3) A method for producing a fluorinated ether compound, comprising
 step 1 of sulfonylating a fluorinated ether compound having a poly(oxyfluoroalkylene) chain and a hydroxy group in the presence of a fluorinated solvent, a base and a sulfonylating agent to obtain a product containing a fluorinated ether compound having a poly(oxyfluoroalkylene) chain and a sulfonate group,
 step 3 of separating the product obtained in step 1 into two phases, and separating and recovering the phase containing a larger amount of the fluorinated ether compound having a poly(oxyfluoroalkylene) chain and a sulfonate group among the two phases, and
 step 4 of contacting the separated and recovered phase with an adsorbent having a pH of at most 8.0.

(4) The method for producing a fluorinated ether compound according to (3), wherein no water washing treatment is performed on the product obtained in step 1 between the end of step 1 and the end of step 4.

(5) The method for producing a fluorinated ether compound according to any one of (1) to (4), wherein the pH of the adsorbent is at most 7.0.

(6) The method for producing a fluorinated ether compound according to any one of (1) to (5), wherein the average particle size of the adsorbent is from 1 to 500 μm.

(7) The method for producing a fluorinated ether compound according to any one of (1) to (6), wherein the specific surface area of the adsorbent is from 30 to 900 $m^2/g$.

(8) The method for producing a fluorinated ether compound according to any one of (1) to (7), wherein the water content of the adsorbent is at most 30 mass %.

(9) The method for producing a fluorinated ether compound according to any one of (1) to (8), wherein the amount of the adsorbent used is from 1 to 100 parts by mass to 100 parts by mass of the fluorinated ether compound having a poly(oxyfluoroalkylene) chain and a hydroxy group.

(10) The method for producing a fluorinated ether compound according to any one of (1) to (9), wherein the fluorinated ether compound having a poly(oxyfluoroalkylene) chain and a hydroxy group is a compound represented by the formula (1) as described later.

Advantageous Effects of Invention

According to the present invention, it is possible to provide a method for producing a fluorinated ether compound having a poly(oxyfluoroalkylene) chain and a sulfonate group, with low impurity content and in high yield.

DESCRIPTION OF EMBODIMENTS

In this specification, a compound represented by the formula (1) is referred to as a compound 1. Compounds represented by other formulas are also referred to in the same manner. A repeating unit represented by the formula (I) is denoted as a unit I. Repeating units represented by other formulas are also denoted in the same manner. A group represented by the formula (2) is denoted as a group 2. Groups represented by other formulas are also denoted in the same manner.

In this specification, when "an alkylene group may have an A group," the alkylene group may have an A group between the carbon-carbon atoms in the alkylene group, or it may have an A group at the terminal, as an alkylene group-A group-.

In this specification, an "aryl group" in an "aryloxy group" includes not only an aryl group but also a heteroaryl group.

In this specification, a "linking group" refers not only to a group of atoms, but also an atom itself may be treated as a "linking group" if it has the function of linking the prescribed groups. For example, a nitrogen atom itself is treated as a trivalent linking group.

The meanings of terms in the present invention are as follows

A "divalent organopolysiloxane residue" is a group represented by the following formula. Rx in the following formula are each independently an alkyl group (preferably a $C_{1-10}$ alkyl group) or a phenyl group. Further, q is an integer of 1 or more, preferably an integer of from 1 to 9, particularly preferably an integer of from 1 to 4.

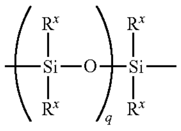

The "number average molecular weight" of a compound is calculated by obtaining the number (average value) of oxyfluoroalkylene groups based on the terminal group by $^{1}H$-NMR and $^{19}F$-NMR.

The first embodiment of the production method of the present invention comprises step 1 of sulfonylating a fluorinated ether compound having a poly(oxyfluoroalkylene) chain and a hydroxy group (hereinafter referred to also as a "specific compound 1") in the presence of a fluorinated solvent, a base and a sulfonylating agent to obtain a product (hereinafter referred to also as a "specific product") containing a fluorinated ether compound having a poly(oxyfluoroalkylene) chain and a sulfonate group (hereinafter referred to also as a "specific compound 2"), and a step 2 of contacting the specific product with an adsorbent having a pH of at most 8.0 (hereinafter referred to also as a "specific adsorbent").

It has been found that according to the above procedure, it is possible to obtain the desired compound (specific compound 2) with low impurity content and in high yield.

The present inventors have found it possible to remove impurities efficiently without decomposing the specific compound 2 obtained in step 1, by bringing the specific product into contact with the specific adsorbent.

In the following, the procedures of the respective steps will be described in detail.

[Step 1]

Step 1 is a step of sulfonylating a specific compound 1 in the presence of a fluorinated solvent, a base and a sulfonylating agent to obtain a specific compound 2.

In the following, the materials to be used in step 1 will first be described in detail, and then, the procedure of the step 1 will be described in detail.

<Fluorinated Solvent>

The fluorinated solvent is a solvent having fluorine atoms.

Specific examples of the fluorinated solvent include a fluorinated alkane, a fluorinated aromatic compound, a fluoroalkyl ether, a fluorinated alkyl amine and a fluoroalcohol.

The fluorinated alkane is preferably a $C_{4-8}$ compound, such as $C_6F_{13}H$ (AC-2000: product name, manufactured by AGC Inc.), $C_6F_{13}C_2H_5$ (AC-6000: product name, manufactured by AGC Inc.) or $C_2F_5CHFCHFCF_3$ (Vertrel: product name, manufactured by DuPont).

Specific examples of the fluorinated aromatic compound include hexafluorobenzene, trifluoromethylbenzene, perfluorotoluene, 1,3-bis(trifluoromethyl)benzene and 1,4-bis(trifluoromethyl)benzene.

The fluoroalkyl ether is preferably a $C_{4-12}$ compound, such as $CF_3CH_2OCF_2CF_2H$ (AE-3000: product name, manufactured by AGC Inc.), $C_4FYOCH_3$ (Novec-7100: product name, manufactured by 3M), $C_4F_9OC_2H_5$ (Novec-7200: product name, manufactured by 3M) or $C_2F_5CF(OCH_3)C_3FY$ (Novec-7300: product name, manufactured by 3M). Specific examples of the fluorinated alkyl amine include perfluorotripropylamine and perfluorotributylamine.

Specific examples of the fluoroalcohol include 2,2,3,3-tetrafluoropropanol, 2,2,2-trifluoroethanol and hexafluoroisopropanol.

As the fluorinated solvent, one type may be used alone, or two or more types may be used in combination.

<Base>

As the base, an organic base and an inorganic base may be mentioned.

Specific examples of the organic base include an alkylamine compound, an arylamine compound, an allylamine compound and a heterocyclic amine compound, and from the viewpoint of their versatility, an alkylamine compound and a heterocyclic amine compound are preferred.

As a specific example of the alkylamine compound, trimethylamine may be mentioned.

Specific examples of the heterocyclic amine compound include pyridine, lutidine, collidine, pyrrole, pyrimidine, N,N-dimethyl-4-aminopyridine, 2,6-dimethylpyridine and 2,6-di-tert-butylpyridine.

Specific examples of the inorganic base include an alkali metal hydride (such as sodium hydride), a carbonate (such as sodium carbonate, potassium carbonate or cesium carbonate), a bicarbonate (such as sodium hydrogen carbonate or potassium hydrogen carbonate), an alkali metal hydroxide (such as sodium hydroxide or potassium hydroxide), and an alkali metal alkoxide (such as potassium tert-butoxide).

As the base, one type may be used alone, or two or more types may be used in combination.

<Sulfonylating Agent>

The sulfonylating agent means a compound capable of replacing the hydroxy group of the target compound with a sulfonate group.

As the sulfonylating agent, for example, a sulfonic acid halide or a sulfonic anhydride may be mentioned.

Specific examples of the sulfonic acid halide include p-toluenesulfonyl chloride, benzenesulfonyl chloride, p-nitrobenzenesulfonyl chloride, 2,4-dinitrobenzenesulfonyl chloride and methanesulfonyl chloride.

Specific examples of the sulfonic anhydride include trifluoromethanesulfonic anhydride, methanesulfonic anhydride, benzenesulfonic anhydride, p-toluenesulfonic anhydride, nitrobenzenesulfonic anhydride, chloromethanesulfonic anhydride and trifluoroacetic anhydride.

<Specific Compound 1>

The specific compound 1 is a compound having a poly(oxyfluoroalkylene) chain and a hydroxy group.

The poly(oxyfluoroalkylene) chain contains a plurality of the following units 1.

Formula (I)

(OX)

X is a fluoroalkylene group having one or more fluorine atoms.

The number of carbon atoms in the fluoroalkylene group is preferably from 1 to 6, more preferably from 2 to 6, particularly more preferably from 2 to 4.

The fluoroalkylene group may be any of linear, branched and cyclic.

The number of fluorine atoms in the fluoroalkylene group is preferably from 1 to 2 times, more preferably from 1.7 to 2 times, the number of carbon atoms, from such a viewpoint that the wear durability and water and oil repellency of the film to be formed from the surface treatment agent produced by using the specific compound 2 will be more excellent.

The fluoroalkylene group is particularly preferably a group in which all hydrogen atoms in the fluoroalkylene group are replaced by fluorine atoms (perfluoroalkylene group).

Specific examples of unit I include $—OCHF—$, $—OCF_2CHF—$, $—OCHFCF_2—$, $—OCF_2CH_2—$, $—OCH_2CF_2—$, $—OCF_2CF_2CHF—$, $—OCHFCF_2CF_2—$, $—OCF_2CF_2CH_2—$, $—OCH_2CF_2CF_2—$, $—OCF_2CF_2CF_2CH_2—$, $—OCH_2CF_2CF_2CF_2—$, $—OCF_2CF_2CF_2CF_2CH_2—$, $—OCH_2CF_2CF_2CF_2CF_2—$, $—OCF_2CF_2CF_2CF_2CF_2CH_2—$, $—OCH_2CF_2CF_2CF_2CF_2CF_2—$, $—OCF_2—$, $—OCF_2CF_2—$, $—OCF_2CF_2CF_2—$, $—OCF(CF_3)CF_2—$, $—OCF_2CF_2CF_2CF_2—$, $—OCF(CF_3)CF_2CF_2—$, $—OCF_2CF_2CF_2CF_2CF_2—$, $—OCF_2CF_2CF_2CF_2CF_2CF_2—$, $—O\text{-cyclo}C_4F_6—$, $—O\text{-cyclo}C_5F_8—$ and $—O\text{-cyclo}C_6F_{10}—$.

Here, $\text{-cyclo}C_4F_6—$ means a perfluorocyclobutanediyl group, and as a specific example of it, a perfluorocyclobutane-1,2-diyl group may be mentioned. -cycloC$_5$FB-means a perfluorocyclopentanediyl group, and as a specific example of it, a perfluorocyclopentane-1,3-diyl group may be mentioned. $\text{-cyclo}C_6F_{10}—$ means a perfluorocyclohexanediyl group, and as a specific example of it, a perfluorocyclohexane-1,4-diyl group may be mentioned.

The number m of repeating unit I in the poly(oxyfluoroalkylene) chain is an integer of 2 or more, preferably an integer of from 2 to 200, more preferably an integer from 5 to 150, further preferably an integer of from 5 to 100, particularly preferably an integer of from 10 to 50.

The poly(oxyfluoroalkylene) chain may contain only one type of (OX) or may contain two or more types of (OX).

The bonding order of two or more types of (OX) is not limited and may be random, alternating or in blocks.

"Containing two or more types of (OX)" means that in the specific compound 1, two or more types of (OX) different in number of carbon atoms are present, two or more types of (OX) different in number of hydrogen atoms are present, two or more types of (OX) different in positions of hydrogen atoms are present, and two or more types of (OX) different in the presence or absence of side chains, or in types of side chains (such as the number of side chains, or the number of carbon atoms in side chains) even if the numbers of carbon atoms are the same.

With respect to the arrangement of two or more types of (OX), for example, the structure represented by $\{(OCF_2)_{m21}\cdot(OCF_2CF_2)_{m22}\}$ represents that m21 $(OCF_2)$ and m22 $(OCF_2CF_2)$ are randomly arranged. Further, the structure represented by $(OCF_2CF_2—OCF_2CF_2CF_2CF_2)_{m25}$ represents that m25 $(OCF_2CF_2)$ and m25 $(OCF_2CF_2CF_2CF_2)$ are arranged alternately.

As $(OX)_m$ representing a poly(oxyfluoroalkylene) chain, $[(OCH_{ma}F_{(2-ma)})_{m11}\cdot(OC_2H_{mb}F_{(4-mb)})_{m12}\cdot(OC_3H_{mc}F_{(6-mc)})_{m13}\cdot(OC_4H_{md}F_{(8-md)})_{m14}\cdot(OCH_{me}F_{(10-me)})_{m15}\cdot(OC_6H_{mf}F_{(12-mf)})_{m16}\cdot(\text{O-CyClo}C_4H_{mg}F_{(6-mg)})_{m17}\cdot(\text{O-)cyclo}C_5H_{mh}F_{(8-m)})_{m18}\cdot(\text{O-cyclO}C_6H_{mi}F_{(10-mi)})_{m19}]$ is preferred. Here, $\text{-cyclo}C_4H_{mg}F_{(6-mg)}$ represents a fluorocyclobutanediyl group, and a fluorocyclobutane-1,2-diyl group is preferred. $\text{-cyclo}C_5H_{mh}F_{(8-mh)}$ represents a fluorocyclopentanediyl group, and a fluorocyclopentane-1,3-diyl group is preferred. $\text{-cyclo}C_6H_{mi}F_{(10-mi)}$ represents a fluorocyclohexanediyl group, and a fluorocyclohexane-1,4-diyl group is preferred.

ma is 0 or 1, mb is an integer of from 0 to 3, mc is an integer of from 0 to 5, md is an integer of from 0 to 7, me is an integer of from 0 to 9, mf is an integer of from 0 to 11, mg is an integer of from 0 to 5, mh is an integer of from 0 to 7, and mi is an integer of from 0 to 9.

m11, m12, m13, m14, m15, m16, m17, m18 and m19 are each independently an integer of at least 0, preferably at most 100.

m11+m12+m13+m14+m15+m16+m17+m18+m19 is an integer of 2 or more, preferably an integer of from 2 to 200, more preferably an integer of from 5 to 150, further preferably an integer of from 5 to 100, particularly preferably an integer of from 10 to 50.

Among them, m12 is preferably an integer of 2 or more, particularly preferably an integer of from 2 to 200.

Further, $C_3H_{mc}F_{(6-mc)}$, $C_4H_{md}F_{(8-md)}$, $C_5H_{me}F_{(10-me)}$ and $C_6H_{mf}F_{(12-mf)}$ may be linear or branched, preferably linear.

Further, the bonding orders of m11 $(OCH_{ma}F_{(2-ma)})$, m12 $(OC_2H_{mb}F_{(4-mb)})$, m13 $(OC_3H_{mc}F_{(6-mc)})$, m14 $(OC_4H_{md}F_{(8-md)})$, m15 $(OC_5H_{me}F_{(10-me)})$, m16 $(OC_6H_{mf}F_{(12-mf)})$, m17 $(\text{O-cyclo}C_4H_{mg}F_{(6-mg)})$, m18 $(\text{O-cyclo}C_5H_{mh}F_{(8-mh)})$ and m19 $(\text{O-cyclo}C_6H_{mi}F_{(10-mi)})$ are not limited.

In a case where m11 is 2 or more, multiple $(OCH_{ma}F_{(2-ma)})$ may be the same or different.

In a case where m12 is 2 or more, multiple $(OC_2H_{mb}F_{(4-mb)})$ may be the same or different.

In a case where m13 is 2 or more, multiple $(OC_3H_{mc}F_{(6-mc)})$ may be the same or different.

In a case where m14 is 2 or more, multiple $(OC_4H_{md}F_{(8-md)})$ may be the same or different.

In a case where m15 is 2 or more, multiple $(OC_5H_{me}F_{(10-me)})$ may be the same or different.

In a case where m16 is 2 or more, multiple $(OC_6H_{mf}F_{(12-mf)})$ may be the same or different.

In a case where m17 is 2 or more, multiple $(\text{O-cyclo}C_4H_{mg}F_{(6-mg)})$ may be the same or different.

In a case where m18 is 2 or more, multiple $(\text{O-cyclo}C_5H_{mh}F_{(8-mh)})$ may be the same or different.

In a case where m19 is 2 or more, multiple $(\text{O-cyclo}C_6H_{mi}F_{(10-mi)})$ may be the same or different.

$(OX)_m$ is preferably those having the following structures.

$\{(OCF_2)_{m21}\bullet(OCF_2CF_2)_{m22}\}$, $(OCF_2CF_2)_{m23}$, $(OCF(CF_3)CF_2)_{m23}$, $(OCF_2CF_2CF_2)_{m24}$, $(OCF_2CF_2—OCF_2CF_2CF_2CF_2)_{m25}$, $\{(OCF_2CF_2CF_2CF_2CF_2)_{m26}\bullet(OCF_2)_{m27}\}$, $\{(OCF_2CF_2CF_2CF_2CF_2)_{m26}\bullet(OCF_2CF_2)_{m27}\}$, $\{(OCF_2CF_2CF_2CF_2CF_2CF_2)_{m26}\bullet(OCF_2)_{m27}\}$, $\{(OCF_2CF_2CF_2CF_2CF_2CF_2)_{m26}\bullet(OCF_2CF_2)_{m27}\}$, $(OCF_2CF_2CF_2CF_2CF_2—OCF_2)_{m28}$, $(OCF_2CF_2CF_2CF_2CF_2—OCF_2CF_2)_{m28}$, -continued $(OCF_2CF_2CF_2CF_2CF_2CF_2—OCF_2)_{m28}$, $(OCF_2CF_2CF_2CF_2CF_2CF_2—OCF_2CF_2)_{m28}$, $(OCF_2—OCF_2CF_2CF_2CF_2CF_2)_{m28}$, $(OCF_2—OCF_2CF_2CF_2CF_2CF_2CF_2)_{m28}$, $(OCF_2CF_2—OCF_2CF_2CF_2CF_2CF_2)_{m28}$, $(OCF_2CF_2—OCF_2CF_2CF_2CF_2CF_2CF_2)_{m28}$.

Here, m21 is an integer of 1 or more, m22 is an integer of 1 or more, and m21+m22 is an integer of from 2 to 500, m23 and m24 are each independently an integer of from 2 to 500, m25 is an integer of from 1 to 250, m26 and m27 are each independently an integer of 1 or more, m26+m27 is an integer of from 2 to 500, and m28 is an integer of from 1 to 250.

$(OX)_m$ more preferably has the following structures from such a viewpoint that specific compound 1 can easily be produced.

$\{(OCF_2)_{m21}\cdot(OCF_2CF_2)_{m22}\}$, $(OCF(CF_3)CF_2)_{m23}$, $(OCF_2CF_2CF_2)_{m24}$, $(OCF_2CF_2)_2\{(OCF_2)_{m21}\cdot(OCF_2CF_2)_{m22-2}\}$, $(OCF_2CF_2—OCF_2CF_2CF_2CF_2)_{m25-1}OCF_2CF_2$, $(OCF_2CF_2CF_2CF_2CF_2—OCF_2)_{m28}$, $(OCF_2CF_2CF_2CF_2CF_2CF_2—OCF_2)_{m28}$, $(OCF_2CF_2—OCF_2CF_2CF_2CF_2CF_2)_{m28-1}OCF_2CF_2$, $(OCF_2CF_2—OCF_2CF_2CF_2CF_2CF_2CF_2)_{m28-1}OCF_2CF_2$.

Here, with respect to m22-2, m25-1 and m28-1, the numbers of m22, m25 and m28 are selected so that they become to be integers of 1 or more.

Among these, $(OX)_m$ is preferably $\{(OCF_2)_{m21}\cdot(OCF_2CF_2)_{m22}\}$ or $(OCF_2CF_2—OCF_2CF_2CF_2CF_2)_{m25-1}OCF_2CF_2$.

In $\{(OCF_2)_{m21}\cdot(OCF_2CF_2)_{m22}\}$, m22/m21 is preferably from 0.1 to 10, more preferably from 0.2 to 5.0, further preferably from 0.2 to 2.0, particularly preferably from 0.2 to 1.5, most preferably from 0.2 to 0.85.

The number average molecular weight of $(OX)_m$ is preferably from 1,000 to 20,000, more preferably from 2,000 to 15,000, particularly preferably from 3,000 to 10,000.

When the average molecular weight is at least the lower limit value, the molecular chain of the specific compound 1 becomes longer, whereby the flexibility of the molecular chain of the specific compound 1 will be improved. This improves the adhesion between the film formed from the surface treatment agent produced using the specific compound 2 and the substrate. As a result, the abrasion resistance of the film will be more excellent. Further, the fluorine content of the film formed from the surface treatment agent produced using the specific compound 2 will be improved, resulting in better water and oil repellency.

Further, when the number average molecular weight is at most the upper limit value, handling efficiency during film deposition will be more excellent.

As the specific compound 1, the following compound 1 is preferred.

Formula (1)

$$A\text{-}(OX)_m\text{-}O\text{-}Z\text{-}(OH)_g$$

A is a perfluoroalkyl group or $\text{-}Q\text{-}(OH)_k$.

The number of carbon atoms in the perfluoroalkyl group is preferably from 1 to 20, more preferably from 1 to 10, further preferably from 1 to 6, particularly preferably from 1 to 3.

The perfluoroalkyl group may be linear or branched.

Specific examples of the perfluoroalkyl group include $CF_3—$, $CF_3CF_2—$, $CF_3CF_2CF_2—$, $CF_3CF_2CF_2CF_2—$, $CF_3CF_2CF_2CF_2CF_2—$, $CF_3CF_2CF_2CF_2CF_2CF_2—$ and $CF_3CF(CF_3)—$.

As the perfluoroalkyl group, $CF_3—$, $CF_3CF_2—$ and $CF_3CF_2CF_2—$ are preferred.

Q is a (k+1)-valent linking group. Here, k is an integer of 1 or more, and as described below, k is preferably an integer of from 1 to 10. Therefore, Q is preferably a 2 to 11-valent linking group.

Q preferably has at least one type of branching point (hereinafter referred to as a "branching point P") selected from the group consisting of C, N, Si, a ring structure and a (k+1)-valent organopolysiloxane residue.

As the ring structure, one type selected from the group consisting of a 3-8 membered aliphatic ring, a 3-8 membered aromatic ring, a 3-8 membered hetero ring, and a fused ring comprising two or more of these rings, is preferred, and the ring structures listed in the formulas below are particularly preferred.

The ring structure may have a substituent such as a halogen atom, an alkyl group (which may contain an etheric oxygen atom between carbon-carbon atoms), a cycloalkyl group, an alkenyl group, an allyl group, an alkoxy group or an oxo group (=O).

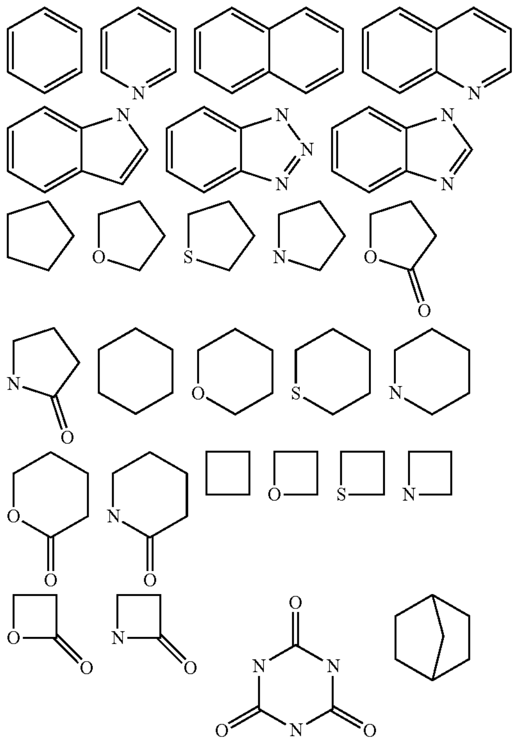

-continued

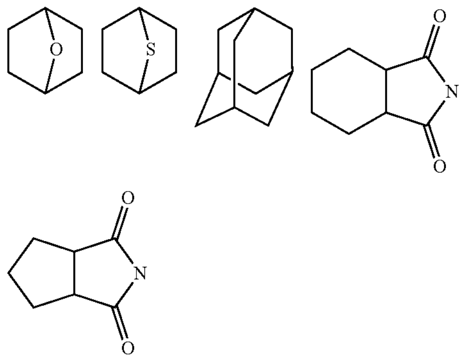

As specific examples of the (k+1)-valent organopolysiloxane residue, the following groups may be mentioned.

Here, $R^5$ in the following formulas is each independently a hydrogen atom, an alkyl group, an alkoxy group or a phenyl group. The number of carbon atoms in the alkyl group and the alkoxy group for $R^5$ is preferably from 1 to 10, particularly preferably 1.

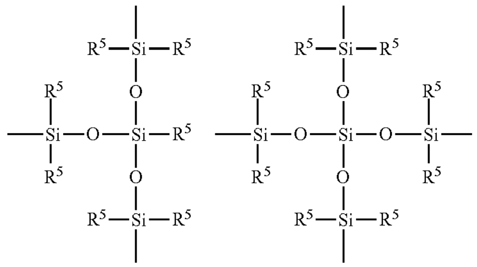

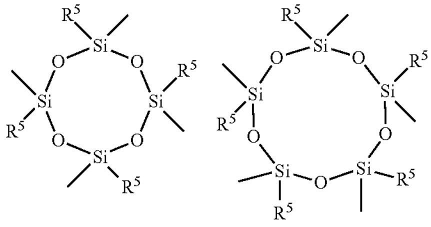

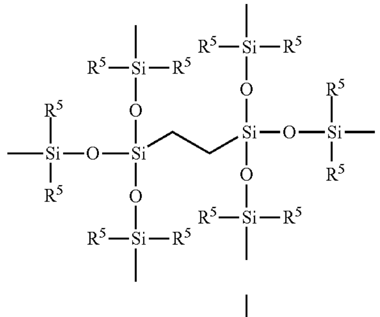

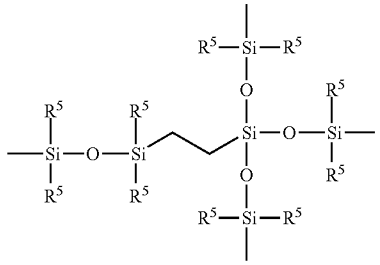

-continued

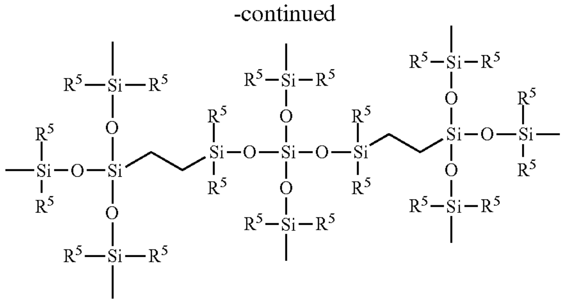

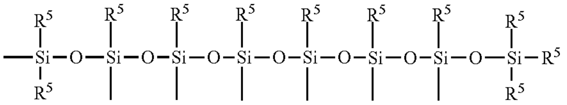

Q may have a group containing at least one type selected from an alkylene group, a fluoroalkylene group, a hydroxyalkylene group, an alkoxyalkylene group, a carbonyl group, an amide bond, an ether bond, a thioether bond, an urea bond, an urethane bond, a carbonate bond, an ester bond, $—SO_2NR^6—$, $—Si(R^6)_2—$, $—OSi(R^6)_2—$, $—Si(CH_3)_2$-Ph-$Si(CH_3)_2—$ and a divalent organopolysiloxane residue.

Here, $R^6$ is a hydrogen atom, a $C_{1-6}$ alkyl group or a phenyl group, and Ph is a phenylene group. The number of carbon atoms in the alkyl group for $R^6$ is preferably from 1 to 3, particularly preferably from 1 to 2, from such a viewpoint that production of the specific compound 1 will be easy.

Further, each bond or group constituting Q may have any of its ends positioned on the A-$(OX)_m$—O side. For example, an amide bond may have a carbon atom positioned on the A-$(OX)_m$—O side, or a nitrogen atom positioned on the A-$(OX)_m$—O side. The same applies to other bonds and groups.

As specific examples of the divalent organopolysiloxane residue, groups of the following formulas may be mentioned. Here, $R^7$ in the following formulas are each independently a hydrogen atom, an alkyl group, an alkoxy group or a phenyl group. The number of carbon atoms in the alkyl group and the alkoxy group for $R^7$ is preferably from 1 to 10, particularly preferably 1.

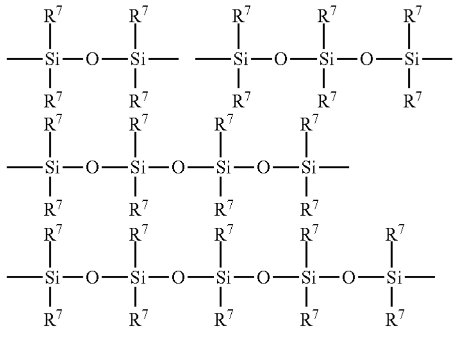

From such a viewpoint that production of the specific compound 1 will be easy, Q preferably has at least one type of bond selected from the group consisting of —C(O)$NR^6$—, —C(O)—, —C(O)$OR^6$—, —$NR^6$— and —O—, particularly preferably has —C(O)$NR^6$—, —O— or —C(O)—.

Q may be a combination of two or more divalent hydrocarbon groups and one or more branching points P, or a combination of two or more hydrocarbon groups, one or more branching points P and one or more bonds B.

Specific examples of the divalent hydrocarbon group include a divalent aliphatic hydrocarbon group (an alkylene group, a cycloalkylene group, etc.) and a divalent aromatic hydrocarbon group (a phenylene group, etc.). The number of carbon atoms in the divalent hydrocarbon group is preferably from 1 to 10, more preferably from 1 to 6, particularly preferably from 1 to 4.

In the compound 1, X is the same as the definition of X in the above unit I, and m is an integer of 2 or more.

Z is a (g+1)-valent linking group.

The definition of Z is the same as the above Q, except that in the above Q, the (k+1) valence is read as the (g+1) valence. In the specific compound 1, Z and Q may be the same or different. From such a viewpoint that production of the specific compound 1 will be easy, it is preferred that Z and Q be the same.

g is an integer of 1 or more, preferably an integer of from 1 to 10, more preferably from 1 to 4, further preferably from 1 to 3.

k is an integer of 1 or more, preferably an integer of from 1 to 4, more preferably from 1 to 3.

As the compound 1, compound 1-11 and compound 1-21 are preferred.

Formula (1-11)

$$A—(OX)_m—O—Y^{11}—(OH)_{g1}$$

Formula (1-21)

$$(OH)_{k1}Y^{22}—(OX)_m—O—Y^{21}—(OH)_{g2}$$

In the formula (1-11), A, X and m are, respectively, the same as the definitions of A, X and m in the formula (1).

$Y^{11}$ is a (g1+1)-valent linking group, and its specific examples are the same as Z in the formula (1).

g1 is an integer of 1 or more, preferably an integer of from 1 to 4, more preferably from 1 to 3.

In the formula (1-21), X and m are, respectively, the same as the definitions of X and m in the formula (1).

k1 is an integer of 1 or more, preferably an integer of from 1 to 4, more preferably from 1 to 3.

$Y^{22}$ is a (k1+1)-valent linking group, and its specific examples are the same as Q in the formula (1).

$Y^{21}$ is a (g2+1)-valent linking group, and its specific examples are the same as Z in the formula (1).

g2 is an integer of 1 or more, preferably an integer of from 1 to 4, more preferably from 1 to 3.

$Y^{11}$ in the formula (1-11) may be the group g2-1 (where d1+d3=1 (i.e. d1 or d3 is 0) and g1=d2+d4, d2+d4≥1), the group g2-2 (where e1=1, g1=e2, e2≥1), group g2-3 (where g1=2), group g2-4 (where h1=1, g1=h2, h2≥1), group g2-5 (where i1=1, g1=i2, i2≥1), group g2-6 (where g1=1), group g2-7 (where g1=3+1), group g2-8 (where g1=4, i4≥1) or group g2-9 (where g1=i5, 5≥1).

Further, $Y^{21}$ and $Y^{22}$ in the formula (1-21) may each independently be group g2-1 (where g2=d2+d4, k1=d2+d4), group g2-2 (where g2=e2, k1=e2), group g2-3 (where g2=2, k1=2), group g2-4 (where g2=h2, k1=h2), group g2-5 (where g2=i2, k1=i2), group g2-6 (where g2=1, k1=1), group g2-7 (where g2=i3+1, k1=i3+1), group g2-8 (where g2=4, k1=4) or group g2-9 (where g2=i5, k1=i).

Formula (g2-1)

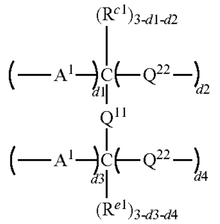

Formula (g2-2)

$$(—A^1—)_{e1}C(R^{e2})_{4-e1-e2}(—Q^{22}—)_{e2}$$

Formula (g2-3)

$$—A^1—N(—Q^{23}—)_2$$

Formula (g2-4)

$$(—A^1—)_{h1}Z^1(—Q^{24}—)_{h2}$$

Formula g2-5)

$$(—A^1—)_{i1}Si(R^{e3})_{4-i1-i2}(—Q^{25}—)_{i2}$$

Formula (g2-6)

$$—A^1—Q^{26}—$$

Formula (g2-7)

$$—A^1—CH(—Q^{22}—)Si(R^{e3})_{3-i3}(—Q^{25}—)_{i3}$$

Formula (g2-8)

$$—A^1—[CH_2C(R^{e4})\ (—Q^{27}—)]_{i4}—R^{e5}$$

Formula (g2-9)

$$—A^1—Z^a(—Q^{28}—)_{i5}$$

Here, in the formula (g2-1) to the formula (g2-9), $A^1$ is bonded to the $(OX)_m$ side, and $Q^{22}$, $Q^{23}$, $Q^{24}$, $Q^{25}$, $Q^{26}$, $Q^{27}$ and $Q^{28}$ are bonded to the OH side.

$A^1$ is a single bond, an alkylene group, a group having —C(O)NR$^6$—, —C(O)—, —OC(O)—, —OC(O)O—, —NHC(O)O—, —NHC(O)NR$^6$—, —O—, —SO$_2$NR$^6$— or —N(R$^6$)SO$_2$— between carbon-carbon atoms of an alkylene group with two or more carbon atoms, or a group having C(O)NR$^6$—, —C(O)—, —OC(O)—, —OC(O)O—, —NHC(O)O—, —NHC(O)NR$^6$—, —O—, —SO$_2$NR$^6$— or —N(R$^6$)SO$_2$— at the terminal on the side opposite to the A side of the alkylene group, and in each formula, if two or more $A^1$ is present, the two or more $A^1$ may be the same or different. The hydrogen atoms of the alkylene group may be replaced by fluorine atoms.

$Q^1$ is a single bond, —O—, an alkylene group, or a group having —C(O)NR$^6$—, —C(O)—, —NR$^6$— or —O— between carbon-carbon atoms of an alkylene group with two or more carbon atoms.

$Q^{22}$ is an alkylene group, or a group having —C(O)NR$^6$—, —C(O)—, —NR$^6$— or —O— between carbon-carbon atoms of an alkylene group with two or more carbon atoms, a group having —C(O)NR$^6$—, —C(O)—, —NR$^6$— or —O— at the terminal on the side not connected to the OH of the alkylene group, or a group having —C(O)NR$^6$—, —C(O)—, —NR$^6$— or —O— between carbon-carbon atoms of an alkylene group with two or more carbon atoms and having —C(O)NR$^6$—, —C(O)—, —NR$^6$— or —O— at the terminal on the side not connected to the OH, and in each formula, if two or more $Q^{22}$ are present, the two or more $Q^{22}$ may be the same or different.

$Q^{23}$ is an alkylene group, or a group having —C(O)NR$^6$—, —C(O)—, —NR$^6$— or —O-between carbon-carbon atoms of an alkylene group with two or more carbon atoms, and the two $Q^{23}$ may be the same or different.

$Q^{24}$ is $Q^{22}$ in a case where the atom at $Z^1$ to which $Q^{24}$ is bonded is a carbon atom, and is $Q^{23}$ in a case where the atom at $Z^1$ to which $Q^{24}$ is bonded is a nitrogen atom, and in each formula, if two or more $Q^{24}$ are present, the two or more $Q^{24}$ may be the same or different.

$Q^{25}$ is an alkylene group, or a group having —C(O)NR$^6$—, —C(O)—, —NR$^6$— or —O-between carbon-carbon atoms of an alkylene group with two or more carbon atoms, and in each formula, if two or more $Q^{26}$ are present, the two or more $Q^{25}$ may be the same or different.

$Q^{26}$ is an alkylene group, or a group having —C(O)NR$^6$—, —C(O)—, —NR$^6$— or —O— between carbon-carbon atoms of an alkylene group with two or more carbon atoms.

$R^6$ is a hydrogen atom, a $C_{1-6}$ alkyl group or a phenyl group.

$Q^{27}$ is a single bond or an alkylene group. If two or more $Q^{27}$ are present, the two or more $Q^{27}$ may be the same or different.

$Q^{23}$ is an alkylene group, or a group having an etheric oxygen atom or a divalent organopolysiloxane residue between carbon-carbon atoms in an alkylene group with two or more carbon atoms. If two or more $Q^{28}$ are present, the two or more $Q^{28}$ may be the same or different.

$Z^1$ is a group having a h1+h2-valent ring structure having a carbon atom or a nitrogen atom to which $A^1$ is directly bonded and having a carbon atom or a nitrogen atom to which $Q^{24}$ is directly bonded.

$R^{e1}$ is a hydrogen atom or an alkyl group, and in each formula, if two or more Rei are present, the two or more Rei may be the same or different.

$R^{e2}$ is a hydrogen atom, a hydroxy group, an alkyl group or an acyloxy group. If two or more $R^{e2}$ are present, the two or more $R^{e2}$ may be the same or different.

$R^{e3}$ is an alkyl group. If two or more $R^{e3}$ are present, the two or more $R^{e3}$ may be the same or different.

$R^{e4}$ is a hydrogen atom or an alkyl group, and a hydrogen atom is preferred from such a viewpoint that the compound can easily be produced. In each formula, if two or more $R^{e4}$ are present, the two or more $R^{e4}$ may be the same or different.

$R^{e5}$ is a hydrogen atom or a halogen atom, and a hydrogen atom is preferred from such a viewpoint that the compound can easily be produced.

d1 is 0 or 1. d2 is an integer of from 0 to 3, preferably 1 or 2. d1+d2 is an integer of from 1 to 3.

d3 is 0 or 1. d4 is an integer of from 0 to 3, preferably 2 or 3. d3+d4 is an integer of from 1 to 3.

d1+d3 is 1.

d2+d4 is in $Y^{11}$ an integer of from 1 to 5, preferably 4 or 5, and in $Y^{21}$ and $Y^{22}$ an integer of from 1 to 5, preferably an integer of from 3 to 5, particularly preferably 4 or 5.

e1+e2 is 3 or 4. e1 is in $Y^{11}$ land in $Y^{21}$ and $Y^{22}$1. e2 is in $Y^{11}$ from 1 to 3, with 2 or 3 being preferred, and in $Y^{21}$ and $Y^{22}$ from 1 to 3, with 2 or 3 being preferred.

h1 is in $Y^{11}$ 1 and in $Y^{21}$ and $Y^{22}$ 1. h2 is in $Y^{11}$ an integer of 1 or more (preferably 2 or 3), and in $Y^{21}$ and $Y^{22}$ an integer of 1 or more (preferably 2 or 3).

i1+i2 is in $Y^{11}$ from 2 to 4 (preferably 3 or 4) and in $Y^{21}$ and $Y^{22}$ an integer of from 2 to 4 (preferably 3 or 4). i1 is in $Y^{11}$ 1 and in $Y^{21}$ and $Y^{22}$ 1. i2 is in $Y^{11}$ an integer of from 1 to 3 (preferably 2 or 3), and in $Y^{21}$ and $Y^{22}$ an integer of from 1 to 3 (preferably 2 or 3).

i3 is an integer of from 0 to 3, preferably from 1 to 3, particularly preferably 2 or 3.

i4 is in $Y^{11}$ one or more (preferably an integer of from 2 to 10, particularly preferably an integer of from 2 to 6), and in $Y^{21}$ and $Y^{22}$ 1 or more (preferably an integer of from 1 to 10, particularly preferably from 1 to 6).

i5 is in $Y^{11}$ 1 or more (preferably an integer of from 2 to 7), and in $Y^{21}$ and $Y^{22}$ 1 or more (preferably an integer of from 2 to 7).

The number of carbon atoms in the alkylene group for $Q^{22}$, $Q^{23}$, $Q^{24}$, $Q^{25}$, $Q^{26}$, $Q^{27}$ and $Q^{28}$ is preferably from 1 to 10, more preferably from 1 to 6, particularly preferably from 1 to 4, from such a viewpoint that production of compounds 1-11 and 1-21 can easily be produced. However, the lower limit value of the number of carbon atoms in the alkylene group in the case where it has a specific bond between carbon-carbon atoms, is 2.

As the ring structure in $Z^1$, the above-mentioned ring structure may be mentioned, and the preferred form is also the same. Since $A^1$ and $Q^{24}$ are directly bonded to the ring structure in $Z^1$, for example, an alkylene group is not linked to the ring structure and $A^1$ and $Q^{24}$ are not linked to that alkylene group.

$Z^a$ is a (i5+1)-valent organopolysiloxane residue, and the following groups are preferred. Here, Ra in the following formulas are each independently an alkyl group (preferably from 1 to 10 carbon atoms) or a phenyl group.

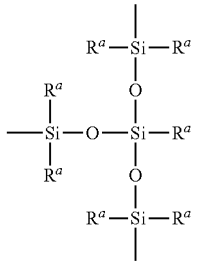

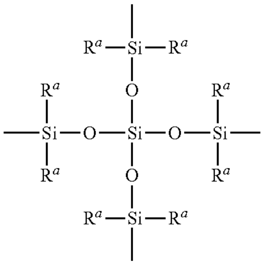

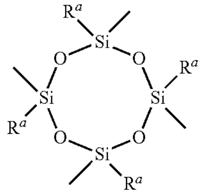

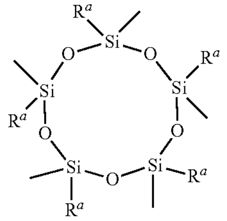

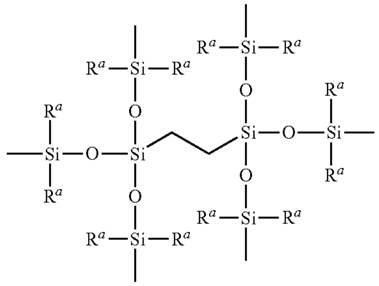

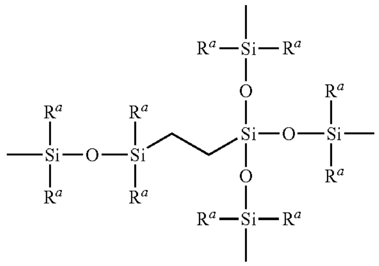

-continued

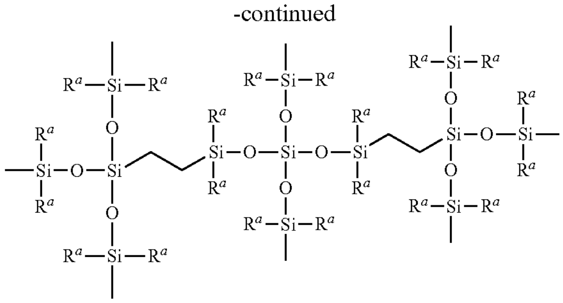

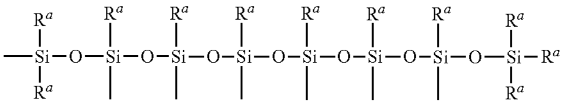

The number of carbon atoms in the alkyl group for $R^{e1}$, $R^{e2}$, $R^{e3}$ or $R^{e4}$ is preferably from 1 to 10, more preferably from 1 to 6, further preferably from 1 to 3, particularly preferably from 1 to 2, from such a viewpoint that compounds 1-11 and 1-21 can be easily produced.

The number of carbon atoms in the alkyl group moiety of the acyloxy group for $R^{e2}$ is preferably from 1 to 10, more preferably from 1 to 6, further preferably from 1 to 3, particularly preferably from 1 to 2, from such a viewpoint that compounds 1-11 and 1-21 can be easily produced.

h1 is preferably from 1 to 6, more preferably from 1 to 4, further preferably 1 or 2, particularly preferably 1, from such a viewpoint that compounds 1-11 and 1-21 can be easily produced.

h2 is preferably from 2 to 6, more preferably from 2 to 4, particularly preferably 2 or 3, from such a viewpoint that compounds 1-11 and 1-21 can be easily produced.

Other forms of $Y^{11}$ may be group g3-1 (where d1+d3=1 (i.e. d1 or d3 is 0), g1=d2×r1+d4×r1), group g3-2 (where e1=1, g1=e2×r1), group g3-3 (where g1=2×r1), group g3-4 (where h1=1, g1=h2×r1), group g3-5 (where i1=1, g1=i2×r1), group g3-6 (where g1=r1), group g3-7 (where g1=r1×(i3+1)), group g3-8 (where g1=r1×i4) and group g3-9 (where g1=r1×i5).

Other forms of $Y^{21}$ and $Y^{22}$ may be group g3-1 (where g2=d2×r1+d4×r1, k1=d2×r1+d4×r1), group g3-2 (where g2=e2×r1, k1=e2×r1), group g3-3 (where g2=2×r1, k1=2×r1), group g3-4 (where g2=h2×r1, k1=h2×r1), group g3-5 (where g2=i2×r1, k1=i2×r1), group g3-6 (where g2=r1, k1=r1), group g3-7 (where g2=r1×(i3+1), k1=r1×(i3+1)), group g3-8 (where g2=r1×4, k1=r1×4) and group g3-9 (where g2=r1×i5, k1=r1×i5).

Formula (g3-1)

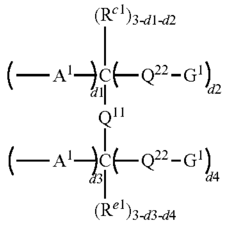

Formula (g3-2)

$$(-A^1-)_{e1}C(R^{e2})_{4-e1-e2}(-Q^{22}-G^1)_{e2}$$

-continued

Formula (g3-3)

$$-A^1-N(-Q^{23}-G^1)_2$$

Formula (g3-4)

$$(-A^1-)_{h1}Z^1(-Q^{24}-G^1)_{h2}$$

Formula (g3-5)

$$(-A^1-)_{i1}Si(R^{e3})_{4-i1-i2}(-Q^{25}-G^1)_{i2}$$

Formula (g3-6)

$$-A^1-Q^{26}-G^1$$

Formula (g3-7)

$$-A^1-CH(-Q^{22}-G^1)-Si(R^{e3})_{3-i3}(-Q^{25}-G^1)_{i3}$$

Formula (g3-8)

$$-A^1-[CH_2C(R^{e4})(-Q^{27}-G^1)_{i4}-R^{e5}$$

Formula (g3-9)

$$-A^1-Z^a(-Q^{28}-G^1)_{i5}$$

Here, in the formulas (g3-1) to (g3-9), $A^1$ is connected to the $(OX)_m$ side and $G^1$ is connected to the OH side.

$G^1$ is group g3, and in each formula, if two or more $G^1$ are present, the two or more $G^1$ may be the same or different. The symbols other than $G^1$ are the same as the symbols in the formulas (g2-1) to (g2-9).

Formula (g3)

$$-Si(R^8)_{3-r1}(-Q^3-)_{r1}$$

Here, in the formula (g3), Si is connected to the $Q^{22}$, $Q^{23}$, $Q^{24}$, $Q^{25}$, $Q^{26}$, $Q^{27}$ and $Q^{28}$ side and $Q^3$ is connected to the OH side. $R^3$ is an alkyl group. $Q^3$ is an alkylene group, or a group having —C(O)NR$^6$—, —C(O)—, —NR$^6$— or —O— between carbon-carbon atoms of an alkylene group with two or more carbon atoms, and two or more $Q^3$ may be the same or different. r1 is 2 or 3. $R^6$ is a hydrogen atom, a $C_{1-6}$ alkyl group or a phenyl group.

The number of carbon atoms in the alkylene group for $Q^3$ is preferably from 1 to 10, more preferably from 1 to 6, particularly preferably from 1 to 4, from such a viewpoint that compound 1-11 and compound 1-21 can easily be produced. However, the lower limit value of the number of carbon atoms in the alkylene group in the case of having a specific bond between carbon-carbon atoms is 2.

The number of carbon atoms in the alkyl group for $R^3$ is preferably from 1 to 10, more preferably from 1 to 6, further preferably from 1 to 3, particularly preferably from 1 to 2, from such a viewpoint that compound 1-11 and compound 1-21 can be easily produced.

As a preferred specific example of Z in the formula (1) ($Y^{11}$ in the formula (1-11), $Y^{21}$ and $Y^{22}$ in the formula (1-21)), an alkylene group which may have —O— between carbon-carbon atoms, or group g2-2 is preferred. Hydrogen atoms of the alkylene group may be replaced by fluorine atoms or hydroxy groups. The number of carbon atoms in the above alkylene group is preferably from 1 to 10, more preferably from 1 to 6.

As a preferred example of —O—Z—$(OH)_g$ in the formula (1), —O—$(CF_2)_{n4}$—$CH_2OH$, or —O—$CF(CF_3)$—$CH_2OH$ may be mentioned. n4 is an integer of 1 or more, preferably from 1 to 6, particularly preferably from 1 to 3.

As compound 1-11 and compound 1-21, for example, the following compounds may be mentioned. In the following formulas, a and b are each independently an integer of 1 or more, preferably an integer of from 1 to 250. c is an integer of 2 or more, preferably an integer of from 2 to 500.

$CF_3(OCF_2)_a(OCF_2CF_2)_bOCF_2CH_2OH$ $CF_3CF_2(OCF_2)_a(OCF_2CF_2)_bOCF_2CH_2OH$ $CF_3CF_2CF_2(OCF_2)_a(OCF_2CF_2)_bOCF_2CH_2OH$ $HOCH_2CF_2(OCF_2)_a(OCF_2CF_2)_bOCF_2CH_2OH$ $CF_3CF_2CF_2(OCF_2CF_2CF_2)_cOCF_2CF_2CH_2OH$ $HOCH_2CF_2CF_2(OCF_2CF_2CF_2)_aOCF_2CF_2(OCF_2CF_2CF_2)_bOCF_2CF_2CH_2OH$ $HOCH_2CF_2CF_2(OCF_2CF_2CF_2)_aOCF_2CF_2CF_2(OCF_2CF_2CF_2)_bOCF_2CF_2CH_2OH$ $HOCH_2CF_2CF_2(OCF_2CF_2CF_2)_aOCF_2CF_2CF_2CF_2(OCF_2CF_2CF_2)_bOCF_2CF_2CH_2OH$ $CF_3CF_2CF_2(OCF(CF_3)CF_2)_cOCF(CF_3)CH_2OH$ $HOCH_2CF(CF_3)(OCF_2CF(CF_3))_aOCF_2CF_2(OCF(CF_3)CF_2)_bOCF(CF_3)CH_2OH$ $HOCH_2CF(CF_3)(OCF_2CF(CF_3))_aOCF_2CF_2CF_2(OCF(CF_3)CF_2)_bOCF(CF_3)CH_2OH$ $HOCH_2CF(CF_3)(OCF_2CF(CF_3))_aOCF_2CF_2CF_2CF_2(OCF(CF_3)CF_2)_bOCF(CF_3)CH_2OH$ $CF_3(OCF_2CF_2OCF_2CF_2CF_2CF_2)_aOCF_2CF_2OCF_2CF_2CF_2CH_2OH$ $CF_3CF_2(OCF_2CF_2OCF_2CF_2CF_2CF_2)_aOCF_2CF_2OCF_2CF_2CF_2CH_2OH$ $HOCH_2CF_2OCF_2OCF_2CF_2CF_2CF_2(OCF_2CF_2OCF_2CF_2CF_2CF_2)_aOCF_2CF_2OCF_2CF_2CH_2OH$ $HOCH_2CF_2CF_2CF_2(OCF_2CF_2OCF_2CF_2CF_2CF_2)_aOCF_2CF_2OCF_2CF_2CH_2CH_2OH$ $CF_3(OCF_2CF_2OCF_2CF_2CF_2CF_2CF_2CF_2)_aOCF_2CF_2OCF_2CF_2CF_2CF_2CF_2CH_2OH$ $CF_3CF_2(OCF_2CF_2OCF_2CF_2CF_2CF_2CF_2CF_2)_aOCF_2CF_2OCF_2CF_2CF_2CF_2CF_2CH_2OH$ $CF_3CF_2CF_2(OCF_2CF_2OCF_2CF_2CF_2CF_2CF_2CF_2)_aOCF_2CF_2OCF_2CF_2CF_2CF_2CF_2CH_2OH$ $HOCH_2CF_2CF_2CF_2CF_2CF_2CF_2(OCF_2CF_2OCF_2CF_2CF_2CF_2CF_2CF_2)_aOCF_2CF_2OCF_2CF_2CF_2CF_2CF_2CH_2OH$

As the specific compound 1, one type may be used alone, or two or more types may be used in combination.

The specific compound 1 can be produced by a known method.

In step 1, other materials other than those mentioned above may be used.

For example, step 1 may be performed in the presence of a phase-transfer catalyst.

Specific examples of the phase transfer catalyst include quaternary ammonium salts such as tetrabutylammonium bromide and benzyltriethylammonium chloride.

<Procedure of Step 1>

In step 1, the above-mentioned respective materials may be mixed all at once or dividedly in small amounts.

The reaction atmosphere in step 1 may be an inert gas atmosphere or an atmospheric air atmosphere.

The reaction temperature in step 1 is preferably from −40 to 200° C., more preferably from −20 to 100° C., particularly preferably from 0 to 50° C.

The reaction time for step 1 is preferably from 0.01 to 40 hours, more preferably from 0.1 to 24 hours, particularly preferably from 0.5 to 10 hours.

The amount of the fluorinated solvent to be used, is preferably from 50 to 500 parts by mass, particularly preferably from 100 to 300 parts by mass, to 100 parts by mass of the specific compound 1, from such a viewpoint that the reaction in step 1 will proceed efficiently.

The molar amount of the base to be used, is preferably from 1.0 to 3.0 times, particularly preferably from 1.3 to 2.0 times, to the molar amount of the specific compound 1, from such a viewpoint that the reaction in step 1 will proceed efficiently.

The molar amount of the sulfonylating agent to be used, is preferably from 1.0 to 3.0 times, particularly preferably from 1.3 to 2.0 times, to the molar amount of the specific compound 1, from such a viewpoint that the reaction in step 1 will proceed efficiently.

By carrying out step 1, the specific compound 1 is sulfonylated, whereby a specific compound 2 will be obtained.

The specific compound 2 has a poly(oxyfluoroalkylene) chain and a sulfonate group. The sulfonate group means a group represented by the formula (A).

$$—OSO_2R$$ Formula (A)

In the above formula, R represents an organic group.

As the organic group, a hydrocarbon group which may have a substituent is preferred.

Specific examples of the hydrocarbon group which may have a substituent include an alkyl group which may have a substituent and an aryl group which may have a substituent.

The number of carbon atoms in the alkyl group is preferably from 1 to 20, more preferably from 2 to 10. Specific examples of the alkyl group include a methyl group, an ethyl group and a tert-butyl group.

The aryl group may have a monocyclic structure or a polycyclic structure. Specific examples of the aryl group include a phenyl group, a naphthyl group and a biphenyl group.

Specific examples of the substituent include a halogen atom such as a fluorine, chlorine, bromine or iodine atom, a nitro group, a nitroso group, a cyano group, an amino group, a hydroxyamino group, a $C_{1-12}$ alkylamino group, a $C_{1-12}$ dialkylamino group, a $C_{7-12}$ aralkylamino group, a $C_{7-12}$ diaralkylamino group, a $C_{1-12}$ alkylsulfonylamino group, a sulfonic acid group, a sulfonamide group, an azide group, a trifluoromethyl group, a carboxyl group, a $C_{1-12}$ acyl group, a $C_{7-12}$ aloyl group, a hydroxy group, a $C_{1-12}$ alkyloxy group, a $C_{7-12}$ aralkyloxy group, a $C_{6-12}$ aryloxy group, a $C_{1-12}$ acyloxy group, a $C_{7-12}$ aroyloxy group, a $C_{3-12}$ silyloxy group, a $C_{1-12}$ alkylsulfonyloxy group, and a $C_{1-12}$ alkylthio group, and the number of substituents may be from 0 to 5.

Specific examples of the sulfonate group include a tosylate group, a mesylate group, a triflate group, and a nonaflate group.

[Step 2]

Step 2 is a step of contacting the specific product with an adsorbent whose pH is at most 8.0. By carrying out step 2, impurities can be removed from the product without decomposing the specific compound 2.

In the following, the materials to be used in step 2 will first be described in detail, and then, the procedure of step 2 will be described in detail.

<Specific Adsorbent>

The specific adsorbent plays a role of contacting the specific product and adsorbing impurities in the product (e.g. base residues, sulfonylating agent residues, etc.).

The pH of the specific adsorbent is at most 8.0. Particularly, at most 7.0 is preferred from the viewpoint that the content of impurities can be more reduced. As the lower limit value of pH of the adsorbent, at least 3.0 is preferred, and at least 5.0 is more preferred, from the viewpoint that the content of impurities can be more reduced.

The method for measuring the pH of a specific adsorbent is as follows.

First, 10 g of the specific adsorbent is added to 100 mL of ion-exchanged water and stirred at 25° C. for 1 hour. Then, the supernatant liquid is separated by centrifugation, and the pH of the supernatant liquid is measured, whereby the pH obtained is adopted as the pH of the specific adsorbent.

The form of the specific adsorbent is often granular.

The average particle size of the specific adsorbent is preferably from 1 to 500 μm, more preferably from 1 to 350 μm, further preferably from 1 to 105 μm, from the viewpoint that the content of impurities can be more reduced.

The average particle size of the specific adsorbent can be obtained by measuring the particle sizes (diameters) of at least 20 pieces of the specific adsorbent and arithmetically averaging them. In a case where the specific adsorbent is a commercial product, the catalog value may be used.

The specific surface area of the specific adsorbent is preferably from 30 to 900 $m^2/g$, more preferably from 200 to 800 $m^2/g$, particularly preferably from 600 to 800 $m^2/g$, from such a viewpoint that the content of impurities can be more reduced.

The specific surface area of the specific adsorbent is determined according to the specific surface area measurement method specified in JIS Z 8830 (2013). In a case where the specific adsorbent is a commercial product, the catalog value may be used.

The water content of the specific adsorbent is preferably at most 30 mass %, more preferably at most 20 mass %, particularly preferably at most 15 mass %, from the viewpoint of excellent yield of the sulfonylated specific compound 1. The lower limit is not particularly restricted, but is often at least 0.1 mass %.

The water content of the adsorbent is the mass fraction of water in the total mass of the adsorbent, and can be measured by the loss on drying method or other methods.

Specific examples of the specific adsorbent include silica, aluminum hydroxide, hydrotalcite, magnesium silicate, aluminum silicate, aluminum oxide, magnesium oxide, and aluminum oxide/magnesium oxide solid solution. These may be used alone or in combination of two or more types.

<Procedure of Step 2>

In step 2, the specific product and the specific adsorbent are brought into contact with each other.

The contacting method may be a method of mixing the specific product and the specific adsorbent, or a method of flowing the specific product through a filter filled with the specific adsorbent.

At the time of contacting the specific product and the specific adsorbent, the specific product and the specific adsorbent may be contacted directly, or a solution in which the specific product is dissolved or dispersed in a solvent may be prepared, and the resulting solution and the specific adsorbent may be contacted.

The solvent to be used may be any solvent that can dissolve or disperse the specific product. An organic solvent is preferred, and a fluorinated solvent is especially preferred. Specific examples of the fluorinated solvent are as described above.

At the time of contacting the specified product and the specified adsorbent, the amount of the specific adsorbent to be used is preferably from 1 to 200 parts by mass, particularly preferably from 1 to 100 parts by mass, to 100 parts by mass of the specific compound 1.

The contact time is preferably from 0.1 to 180 minutes, particularly preferably from 1 to 60 minutes, from such a viewpoint that the content of impurities can be more reduced.

The temperature at the time of contact is preferably from 0 to 40° C., particularly preferably from 10 to 30° C., from such a viewpoint that the content of impurities can be more reduced.

Further, it is preferred that no water washing treatment be performed on the specific product between the end of step 1 and the end of step 2. If a water washing treatment is performed on the specific product, there is a risk that the specific compound 2 in the specific product may decompose, and as a result, there is a concern that the yield may decrease.

Here, the water washing treatment means a treatment in which the specific product is brought into contact with an aqueous solution. The aqueous solution to be used in the water washing treatment may contain a salt or other substances.

Furthermore, step 1 and step 2 do not have to be performed in succession. That is, step 2 may be carried out following step 1, or step 2 may be carried out after carrying out some steps after step 1. In the latter case, for example, after obtaining the specific compound 2 and producing a fluorinated ether compound having a poly(oxyfluoroalkylene) chain and a reactive silyl group, step 2 may be carried out. Otherwise, for example, after obtaining the specific compound 2 and producing a fluorinated ether compound having a poly(oxyfluoroalkylene) chain and a group (e.g. allyl group) to which a reactive silyl group can be introduced, step 2 may be carried out to introduce a reactive silyl group and produce a poly(oxyfluoroalkylene) chain and a reactive silyl group.

The second embodiment of the production method of the present invention comprises step 1 of sulfonylating the specific compound 1 in the presence of a fluorinated solvent, a base and a sulfonylating agent to obtain a specific product, step 3 of separating the specific product into two phases, and separating and recovering the phase with a higher content of the specific compound 2 among the two phases, and step 4 of contacting the separated and recovered phase with an adsorbent having a pH of at most 8.0.

By carrying out step 3, the yield of fluorinated ether compound having a poly(oxyfluoroalkylene) chain and a sulfonate group will be more excellent.

Since the procedure of step 1 in the above second embodiment is the same as the procedure of step 1 in the first embodiment, its description is omitted.

In step 3, as the method of separating the specific product into two phases, a method of allowing the specific product to stand still may be mentioned. The temperature at the time of allowing it to stand still is preferably from 0 to 50° C.

Next, among the specific products separated into two phases, the phase with a higher content of the specific compound 2 is recovered. For example, in a case where the phase with a higher content of the specific compound 2 is the lower phase, only the lower phase is recovered.

The procedure in step 4 is the same procedure as in the above step 2, except that the phase separated and recovered in step 3 is used instead of the specific product, and therefore, its description is omitted.

Further, it is preferred that no water washing treatment be performed on the specific product between the end of step 1 and the end of step 4 above. If a water washing treatment is performed on the specific product, there is a risk that the specific compound 2 in the specific product may decompose, and as a result, there is a concern that the yield may decrease.

Here, the water washing treatment means a treatment in which the specific product is brought into contact with an aqueous solution. The aqueous solution to be used in the water washing treatment may contain a salt or other substances.

Compound 2 is preferred as the specific compound 2 produced by the above production method of the present invention (first embodiment and second embodiment).

Formula (2)

$$A^1—(OX)_m—O—Z—(OSO_2R)_g$$

X, Z, m and g in the formula (2) are, respectively, the same as the definitions of X, Z, m and g in the formula (1).

R in the formula (2) is the same as the definition of R in the formula (A).

$A^1$ is a perfluoroalkyl group or $-Q-(OSO_2R)_k$.

The definition of the perfluoroalkyl group is the same as the definition of the perfluoroalkyl group of A in the formula (1). Q and k are the same as the definitions of Q and k in the formula (1).

Further, as the compound 2, compound 2-11 and compound 2-2 are also preferred.

Formula (2-11)

$$A—(OX)_m—O—Y^{11}—(OSO_2R)_{g1}$$

Formula (2-21)

$$(RSO_2O)_{k1}Y^{22}—(OX)_m—O—Y^{21}—(OSO_2R)_{g2}$$

A, X, $Y^{11}$, m and g1 in the formula (2-11) are, respectively, the same as the definitions of A, X, $Y^{11}$, m and g1 in the formula (1-11).

R in the formula (2-11) is the same as the definition of R in the formula (A).

$Y^{22}$, X, $Y^{21}$, k1, m, and g2 in the formula (2-21) are, respectively, the same as the definitions of $Y^{22}$, X, $Y^{21}$, k1, m and g2 in the formula (1-11).

R in the formula (2-21) is the same as the definition of R in the formula (A).

The fluorinated ether compound having a poly(oxyfluoroalkylene) chain and a sulfonate group produced by the production method of the present invention as described above (first embodiment and second embodiment) is useful as an intermediate for producing a fluorinated ether compound having a poly(oxyfluoroalkylene) chain and a reactive silyl group.

For example, a fluorinated ether compound having a poly(oxyfluoroalkylene) chain and a reactive silyl group can be produced by using a sulfonated specific compound 1 produced according to the method described in Patent Document 1.

EXAMPLES

In the following, the present invention will be described in detail with reference to Examples. Ex. 1 to 9 and Ex. 15 to 19 are Examples of the present invention, and Ex. 10 to 14 are Comparative Examples. However, the present invention is not limited to these Examples. Further, the amounts of the respective components in Tables given below are shown on a mass basis.

The adsorbents to be used in Ex. 1 to 14 are as follows

Silica gel D-75-60A(N) (manufactured by AGC Si-Tech Co., Ltd., average particle size: 72 μm, specific surface area: 751 $m^2/g$, water content: 6.9 mass %)

Silica gel D-75-60A (manufactured by AGC Si-Tech Co., Ltd., average particle size: 74 μm, specific surface area: 709 $m^2/g$, water content: 6.7 mass %)

KYOWAAD 200 (manufactured by Kyowa Chemical Industry Co., Ltd., average particle size: 318 μm, specific surface area 211 $m^2/g$, water content: 18.8 mass %)

KYOWAAD 700 (manufactured by Kyowa Chemical Industry Co., Ltd., average particle size: 261 μm, specific surface area 206 $m^2/g$, water content: 15.6 mass %)

KYOWAAD 500 (manufactured by Kyowa Chemical Industry Co., Ltd., average particle size: 273 μm; specific surface area: 201 m2/g, water content: 3.3 mass %)

KW-2000 (manufactured by Kyowa Chemical Industry Co., Ltd, average particle size: 48 μm, specific surface area: 190 $m^2/g$, water content: 14.9 mass %)

Alumina (manufactured by FUJIFILM Wako Pure Chemical Corporation, average particle size: 126 μm, specific surface area: 539 $m^2/g$, water content: 7.8 mass %)

[Ex. 1]

In a 200-mL round bottom flask made of glass, 50.0 g of compound (1-1) being specific compound 1, 50.1 g of AE-3000, 1.63 g of 2,6-dimethylpyridine (2,6-lutidine) and 4.25 g of trifluoromethanesulfonic anhydride were put, and the mixed liquid was stirred for 1 hour at room temperature under a nitrogen atmosphere. After completion of the reaction, the mixed liquid was left to stand so that two phases were separated, whereupon the lower phase was recovered. The recovered lower phase was filtered through 25.0 g of silica gel D-75-60A(N) and further washed with 150 g of AE-3000. AE-3000 was distilled off from the mixed liquid, to obtain 49.8 g (recovery rate: 93%, purity: 99.9%) of the product containing compound (2-1).

(1-1)
$$CF_3—O—(CF_2CF_2OCF_2CF_2CF_2CF_2O)_x—CF_2CF_2OCF_2CF_2CF_2CH_2—OH$$

(2-1)
$$CF_3—O—(CF_2CF_2OCF_2CF_2CF_2CF_2O)_x—CF_2CF_2OCF_2CF_2CF_2CH_2—OSO_2CF_3$$

x represents the repeating number, and the repeating number in the compound used in this Ex. was 14.0.

[Ex. 2 to 5, Ex. 10 to 13].

A product containing compound (2-1) was obtained in accordance with the same procedure as in Ex. 1, except that instead of silica gel D-75-60A(N), the adsorbent and the fluorinated solvent listed in Tables 1 and 2 were used.

[Ex. 6]

A product containing compound (2-1) was obtained in accordance with the same procedure as in Ex. 1, except that without leaving the mixed liquid to stand to separate it into two phases, the obtained resulting mixture was filtered through silica gel D-75-60A(N), and the amount of the adsorbent used was changed as shown in Table 1.

[Ex. 7 to 9]

A product containing compound (2-1) was obtained in accordance with the same procedure as in Ex. 6, except that instead of silica gel D-75-60A(N), the adsorbent listed in Table 1 was used, and the amount of the adsorbent used was changed as shown in Table 1.

[Ex. 14]

In a 200-mL round bottom flask made of glass, 50.0 g of compound (1-1) being specific compound 1, 50.1 g of 1,3-bis(trifluoromethyl)benzene, 1.63 g of triethylamine and 4.25 g of trifluoromethanesulfonic anhydride were put, and the mixed liquid was stirred for 1 hour at room temperature under a nitrogen atmosphere. The obtained mixture was washed with water, and the organic phase was recovered. From the recovered organic phase, 1,3-bis(trifluoromethyl) benzene was distilled off to obtain a product containing compound (2-1).

Example 15

In a 200-mL round bottom flask made of glass, 50.0 g of compound (1-2) being specific compound 1, 50.0 g of AE-3000, 1.64 g of 2,6-dimethylpyridine (2,6-lutidine) and 4.25 g of trifluoromethanesulfonic anhydride were put, and the mixed liquid was stirred for 1 hour at room temperature under a nitrogen atmosphere. After completion of the reaction, a product containing compound (2-2) was obtained in accordance with the same procedure as in Ex. 1 except that instead of silica gel D-75-60A(N), silica gel D-75-60A was used.

(1-2)
$$CF_3(OCF_2)_a(OCF_2CF_2)_bOCF_2CH_2—OH$$

(2-2)
$$CF_3(OCF_2)_a(OCF_2CF_2)_bOCF_2CH_2—OSO_2CF_3$$

a and b represent the repeating numbers, and the repeating numbers for the compound used in this Ex. were a=28.0 and b=17.0. Further, the order of presence of ($OCF_2$) and ($OCF_2CF_2$) is arbitrary.

[Ex. 16]

In a 200-mL round bottom flask made of glass, 50.0 g of compound (1-3) being specific compound 1, 50.0 g of AE-3000, 3.27 g of 2,6-dimethylpyridine (2,6-lutidine) and 8.50 g of trifluoromethanesulfonic anhydride were put, and the mixed liquid was stirred for 1 hour at room temperature under a nitrogen atmosphere. After completion of the reaction, a product containing compound (2-3) was obtained in accordance with the same procedure as in Ex. 15.

(1-3)
$$HOCH_2CF_2(OCF_2)_a(OCF_2CF_2)_bOCF_2CH_2—OH$$

(2-3)
$$CF_3SO_2O—CH_2CF_2(OCF_2)_a(OCF_2CF_2)_bOCF_2CH_2—OSO_2CF_3$$

a and b represent the repeating numbers, and the repeating numbers for the compound used in this Ex. were a=28.0 and b=17.0. The order of presence of ($OCF_2$) and ($OCF_2CF_2$) is arbitrary.

[Ex. 17]

In a 200-mL round bottom flask made of glass, 50.0 g of compound (1-4) being specific compound 1, 50.1 g of AE-3000, 1.64 g of 2,6-dimethylpyridine (2,6-lutidine) and 4.25 g of trifluoromethanesulfonic anhydride were put, and the mixed liquid was stirred for 1 hour at room temperature under a nitrogen atmosphere. After completion of the reaction, a product containing compound (2-4) was obtained in accordance with the same procedure as in Ex. 15.

(1-4)
$$CF_3CF_2CF_2(OCF(CF_3)CF_2)_cOCF(CF_3)CH_2—OH$$

(2-4)
$$CF_3CF_2CF_2(OCF(CF_3)CF_2)_cOCF(CF_3)CH_2—OSO_2CF_3$$

c represents the repeating number, and the repeating number for the compound used in this Ex. was 28.0.

[Ex. 18]

In a 200-mL round bottom flask made of glass, 50.0 g of compound (1-5) being specific compound 1, 50.0 g of AE-3000, 1.63 g of 2,6-dimethylpyridine (2,6-lutidine) and 4.26 g of trifluoromethanesulfonic anhydride were put, and the mixed liquid was stirred for 1 hour at room temperature under a nitrogen atmosphere. After completion of the reaction, a product containing compound (2-5) was obtained in accordance with the same procedure as in Ex. 15.

(1-5)
$$CF_3CF_2CF_2(OCF_2CF_2CF_2)_cOCF_2CF_2CH_2—OH$$

(2-5)
$$CF_3CF_2CF_2(OCF_2CF_2CF_2)_cOCF_2CF_2CH_2—OSO_2CF_3$$

c represents the repeating number, and the repeating number for the compound used in this Ex. was 30.0.

[Ex. 19]

In a 200-mL round bottom flask made of glass, 50.0 g of compound (1-6) being specific compound 1, 50.0 g of AE-3000, 3.26 g of 2,6-dimethylpyridine (2,6-lutidine) and 8.52 g of trifluoromethanesulfonic anhydride were put, and the mixed liquid was stirred for 1 hour at room temperature under a nitrogen atmosphere. After completion of the reaction, a product containing compound (2-6) was obtained in accordance with the same procedure as in Ex. 15.

$$HOCH_2CF_2CF_2CF_2(OCF_2CF_2OCF_2CF_2CF_2CF_2)_aOCF_2CF_2OCF_2CF_2CF_2CH_2{-}OH \quad (1\text{-}6)$$

$$CF_3SO_2O{-}CH_2CF_2CF_2CF_2(OCF_2CF_2OCF_2CF_2CF_2)_aOCF_2CF_2OCF_2CF_2CF_2CH_2{-}OSO_2CF_3 \quad (2\text{-}6)$$

a represents the repeating number, and the repeating number for the compound used in this Ex. was 10.0.

In Tables 1 to 3, in the column for "Step 3", "0" means a case where the above step 3 was carried out, and "x" means a case where the step 3 was not carried out.

In Tables 1 to 3, in the column for "Post-reaction water washing", "No" means a case where no water washing was performed on the product obtained in step 1, and "Yes" means a case where water washing was performed, between the end of step 1 and the end of step 2 or between the end of step 1 and the end of step 4.

In Tables 1 to 3, "pH of adsorbent" represents the pH of the adsorbent. The method for measuring the pH of a specific adsorbent is as described above.

In Tables 1 to 3, "Amount of adsorbent" represents the ratio of the amount of the adsorbent used to the amount of specific compound 1 used as raw material (amount of adsorbent used (wt)/amount of specific compound 1 used (wt)).

In Tables 1 to 3, the column for "Recovery rate" represents the proportion (%) of the molar amount of the obtained specific compound 2 to the charged amount (molar amount) of the specific compound 1 as raw material.

In Tables 1 to 3, the column for "Decomposition of desired product" indicates the decomposition rate of the specific compound 2 in the obtained product [{molar amount of decomposed specific compound 2/(molar amount of decomposed specific compound 2+molar amount of specific compound 2 that was not decomposed)}×100], and "◎" represents a decomposition rate of 0%, "○" represents a decomposition rate of more than 0% and at most 0.1%, "Δ" represents a decomposition rate of more than 0.1% and at most 0.5%, and "x" represents a decomposition rate of more than 0.5%.

In Tables 1 to 3, the column for "Impurity residual amount" indicates the impurity residual rate of impurities other than specific compound 1 in the obtained product {(molar amount of impurities/molar amount of product)×100}, and "◎" represents an impurity residue rate of 0%, "○" indicates an impurity residue rate of more than 0% and at most 0.1%, "Δ" represents an impurity residue rate of more than 0.1% and at most 0.5%, and "x" represents an impurity residue rate of more than 0.5%.

TABLE 1

| | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Fluorinated solvent | AE-3000 | AE-3000 | AE-3000 | AE-3000 | AC-2000 | AE-3000 | AE-3000 | AE-3000 | AE-3000 |
| Base | 2,6-lutidiine | 2,6-lutidiine | 2,6-lutidiine | 2,6-lutidiine | 2,6-lutidiine | 2,6-lutidiine | 2,6-lutidiine | 2,6-lutidiine | 2,6-lutidiine |
| Step 3 | ○ | ○ | ○ | ○ | ○ | x | x | x | x |
| Post-reaction water washing | No | No | No | No | No | No | No | No | No |
| Type of adsorbent | Silica gel D-75-60A(N) | Silica gel D-75-60A | KYOWAAD 200 | KYOWAAD 700 | KYOWAAD 700 | Silica gel D-75-60A(N) | Silica gel D-75-60A | KYOWAAD 200 | KYOWAAD 700 |
| Component of adsorbent | $SiO_2$ | $SiO_2$ | $Al(OH)_3{\cdot}mH_2O$ | $Al_2O_3{\cdot}9SiO_2{\cdot}mH_2O$ | $Al_2O_3{\cdot}9SiO_2{\cdot}mH_2O$ | $SiO_2$ | $SiO_2$ | $Al(OH)_3{\cdot}mH_2O$ | $Al_2O_3{\cdot}9SiO_2{\cdot}mH_2O$ |
| pH of adsorbent | 7.3 | 6.8 | 7.5 | 7.5 | 7.5 | 7.3 | 6.8 | 7.5 | 7.5 |
| Amount of adsorbent | 0.5 wt/wt | 0.5 wt/wt | 0.5 wt/wt | 0.5 wt/wt | 0.5 wt/wt | 1.0 wt/wt | 1.0 wt/wt | 0.5 wt/wt | 1.0 wt/wt |
| Recovery rate | 93% | 97% | 96% | 95% | 95% | 82% | 86% | 84% | 84% |
| Decomposition of desired product | ○ | ◎ | ○ | ○ | ○ | ○ | ◎ | ○ | ○ |
| Impurity residual amount | ○ | ◎ | ○ | ○ | ○ | ○ | ◎ | ○ | ○ |

TABLE 2

| | Ex. 10 | Ex. 11 | Ex. 12 | Ex. 13 | Ex. 14 |
|---|---|---|---|---|---|
| Fluorinated solvent | AE-3000 | AC-2000 | AE-3000 | AE-3000 | 1,3-bis(trifluoromethyl) benzene |
| Base | 2,6-lutidiine | 2,6-lutidiine | 2,6-lutidiine | 2,6-lutidiine | Trimethylamine |
| Step 3 | ○ | ○ | ○ | ○ | x |
| Post-reaction water washing | No | No | No | No | Yes |
| Adsorbent | KYOWAAD 500 | KYOWAAD 500 | KW-2000 | Alumina | — |
| Component | $Mg_6Al_2(OH)_{16}CO_3{\cdot}mH_2O$ | $Mg_6Al_2(OH)_{16}CO_3{\cdot}mH_2O$ | $Mg_{0.7}Al_{0.3}O_{1.15}$ | $Al_2O_3$ | — |
| pH of adsorbent | 9.3 | 9.3 | 10.5 | 10.0 | — |
| Amount of adsorbent | 0.5 wt/wt | 0.5 wt/wt | 0.5 wt/wt | 0.5 wt/wt | — |
| Recovery rate | 34% | 30% | 37% | 43% | 99% |

TABLE 2-continued

| | Ex. 10 | Ex. 11 | Ex. 12 | Ex. 13 | Ex. 14 |
|---|---|---|---|---|---|
| Decomposition of desired product | x | x | x | Δ | Δ |
| Impurity residual amount | Δ | Δ | Δ | Δ | x |

TABLE 3

| | Ex. 15 | Ex. 16 | Ex. 17 | Ex. 18 | Ex. 19 |
|---|---|---|---|---|---|
| Fluorinated solvent | AE-3000 | AE-3000 | AE-3000 | AE-3000 | AE-3000 |
| Base | 2,6-lutidiine | 2,6-lutidiine | 2,6-lutidiine | 2,6-lutidiine | 2,6-lutidiine |
| Step 3 | ○ | ○ | ○ | ○ | ○ |
| Post-reaction water washing | No | No | No | No | No |
| Type of adsorbent | Silica gel D-75-60A | Silica gel D-75-60A | Silica gel D-75-60A | Silica gel D-75-60A | Silica gel D-75-60A |
| Component of adsorbent | $SiO_2$ | $SiO_2$ | $SiO_2$ | $SiO_2$ | $SiO_2$ |
| pH of adsorbent | 6.8 | 6.8 | 6.8 | 6.8 | 6.8 |
| Amount of adsorbent | 0.5 wt/wt | 0.5 wt/wt | 0.5 wt/wt | 0.5 wt/wt | 0.5 wt/wt |
| Recovery rate | 97% | 96% | 95% | 95% | 96% |
| Decomposition of desired product | ◎ | ◎ | ◎ | ◎ | ◎ |
| Impurity residual amount | ◎ | ◎ | ◎ | ◎ | ◎ |

As shown in Tables 1, 2 and 3, it has been confirmed that according to the production method of the present invention, it is possible to obtain the desired effect.

In particular, it has been confirmed that as in Ex. 2, Ex. 7 and Ex. 15 to 19, in a case where the pH of the adsorbent is at most 7.0, the effect is superior.

This application is a continuation of PCT Application No. PCT/JP2021/033804, filed on Sep. 14, 2021, which is based upon and claims the benefit of priority from Japanese Patent Application No. 2020-155282 filed on Sep. 16, 2020. The contents of those applications are incorporated herein by reference in their entireties.

What is claimed is:

1. A method for producing a fluorinated ether compound, comprising step 1 of sulfonylating a fluorinated ether compound having a poly(oxyfluoroalkylene) chain and a hydroxy group in the presence of a fluorinated solvent, a base and a sulfonylating agent to obtain a product containing a fluorinated ether compound having a poly(oxyfluoroalkylene) chain and a sulfonate group, and step 2 of contacting the product obtained in step 1 with an adsorbent having a pH of at most 8.0, thereby obtaining the fluorinated ether compound; wherein:

the adsorbent comprises at least one selected from the group consisting of silica, aluminum hydroxide, hydrotalcite, magnesium silicate, aluminum silicate, aluminum oxide, magnesium oxide, and aluminum oxide/magnesium oxide solid solution;

the adsorbent has a specific surface area of from 30 to 900 $m^2/g$;

the amount of the adsorbent used is from 1 to 100 parts by mass relative to 100 parts by mass of the fluorinated ether compound having a poly(oxyfluoroalkylene) chain and a hydroxy group; and the fluorinated ether compound having a poly(oxyfluoroalkylene) chain and a hydroxy group is a compound represented by Formula (1);

$$A—(OX)_m—O—Z—(OH)_g \qquad \text{Formula (1)}$$

where A is a perfluoroalkyl group or $-Q-(OH)_k$,

Z is a (g+1)-valent linking group,

X is a fluoroalkylene group having one or more fluorine atoms, m is an integer of at least 2, g is an integer of at least 1, Q is a (k+1)-valent linking group, and k is an integer of at least 1.

2. The method for producing a fluorinated ether compound according to claim 1, wherein no water washing treatment is performed on the product obtained in step 1 between the end of step 1 and the end of step 2.

3. A method for producing a fluorinated ether compound, comprising step 1 of sulfonylating a fluorinated ether compound having a poly(oxyfluoroalkylene) chain and a hydroxy group in the presence of a fluorinated solvent, a base and a sulfonylating agent to obtain a product containing a fluorinated ether compound having a poly(oxyfluoroalkylene) chain and a sulfonate group, step 3 of separating the product obtained in step 1 into two phases, and separating and recovering the phase containing a larger amount of the fluorinated ether compound having a poly(oxyfluoroalkylene) chain and a sulfonate group among the two phases, and step 4 of contacting the separated and recovered phase with an adsorbent having a pH of at most 8.0, thereby obtaining the fluorinated ether compound;

wherein:

the adsorbent comprises at least one selected from the group consisting of silica, aluminum hydroxide, hydrotalcite, magnesium silicate, aluminum silicate, aluminum oxide, magnesium oxide, and aluminum oxide/magnesium oxide solid solution;

the adsorbent has a specific surface area of from 30 to 900 $m^2/g$;

the amount of the adsorbent used is from 1 to 100 parts by mass relative to 100 parts by mass of the fluorinated ether compound having a poly(oxyfluoroalkylene) chain and a hydroxy group; and the fluorinated ether compound having a poly(oxyfluoroalkylene) chain and a hydroxy group is a compound represented by Formula (1):

$$A—(OX)_m—O—Z—(OH)_g \quad \text{Formula (1)}$$

where A is a perfluoroalkyl group or -Q-$(OH)_k$,

Z is a (g+1)-valent linking group,

X is a fluoroalkylene group having one or more fluorine atoms, m is an integer of at least 2, g is an integer of at least 1, Q is a (k+1)-valent linking group, and k is an integer of at least 1.

4. The method for producing a fluorinated ether compound according to claim 3, wherein no water washing treatment is performed on the product obtained in step 1 between the end of step 1 and the end of step 4.

5. The method for producing a fluorinated ether compound according to claim 1, wherein the pH of the adsorbent is at most 7.0.

6. The method for producing a fluorinated ether compound according to claim 1, wherein the average particle size of the adsorbent is from 1 to 500 μm.

7. The method for producing a fluorinated ether compound according to claim 1, wherein the water content of the adsorbent is at most 30 mass %.

* * * * *